United States Patent [19]
Orr et al.

[11] Patent Number: 5,608,157
[45] Date of Patent: Mar. 4, 1997

[54] METHOD AND APPARATUS FOR MEASURING ENVELOPE DENSITY

[75] Inventors: Clyde Orr, Dunwoody; Ronnie W. Camp, Duluth, both of Ga.

[73] Assignee: Micromeritics Instrument Corporation, Norcross, Ga.

[21] Appl. No.: 544,591

[22] Filed: Oct. 18, 1995

[51] Int. Cl.$^6$ ............................. G01N 9/00; G01F 17/00
[52] U.S. Cl. ............................. 73/32 R; 73/433; 73/149
[58] Field of Search ................................... 73/32 R, 433, 73/437, 38, 149, 813, 818, 823, 824, 825

[56] References Cited

U.S. PATENT DOCUMENTS

| | | | |
|---|---|---|---|
| 2,667,782 | 2/1954 | Shea | 73/149 |
| 2,706,908 | 4/1955 | MacRoberts | 73/149 |
| 3,060,724 | 10/1962 | Smith, Jr. et al. | 73/32 |
| 3,129,585 | 4/1964 | Hamilton | 73/149 |
| 3,246,504 | 4/1966 | Halff et al. | 73/32 |
| 3,309,912 | 3/1967 | Boland et al. | 73/38 |
| 3,741,011 | 6/1973 | Seybold | 73/149 |
| 4,112,738 | 9/1978 | Turner | 73/32 R |
| 4,154,098 | 5/1979 | Pelletier | 73/149 |
| 4,196,618 | 4/1980 | Patterson | 73/149 |
| 4,224,821 | 9/1980 | Taylor et al. | 73/32 R |
| 4,283,148 | 8/1981 | Peterson | 366/142 |
| 4,361,052 | 11/1982 | Nicol et al. | 73/863 |
| 4,699,002 | 10/1987 | Rockley | 73/153 |
| 5,323,655 | 6/1994 | Eagan et al. | 73/432.1 |

FOREIGN PATENT DOCUMENTS

| | | |
|---|---|---|
| 1959681 | 11/1969 | Germany . |
| 108512 | 8/1917 | United Kingdom . |

OTHER PUBLICATIONS

B. Buczek, "Measurement of the Apparent Density of Porous Particles by a Powder Characteristics Tester," Proceedings of Second World Congress Particle Technology, Sep. 19–22, 1990 Kyoto, Japan, pp. 103–109.

Brochure entitled "A Tool for Solid Body Open Porosity Measurement," by Tenakon Research Industrial Corp. (undated).

ASTM Designation: C 830–83 "Standard Test Methods for Apparent Porosity, Liquid Absorption, Apparent Specific Gravity, and Bulk Density of Burned Refractory Brick and Shapes by Vacuum Pressure," Jan. 1984, pp. 247–249.

ASTM Designation: C 493–86 "Standard Test Methods for Bulk Density and Porosity of Granular Refractory Materials by Mercury Displacement," Sep. 1986, pp. 125–127.

ASTM Designation: C 20–87 "Standard Test Methods for Apparent Porosity, Water Absorption, Apparent Specific Gravity, and Bulk Density of Burned Refractory Brick and Shapes by Boiling Water," Aug. 1987, pp. 5–7.

ASTM Designation: C 914–89 "Standard Test Method for Bulk Density and Volume of Solid Refractories by Wax Immersion," Aug. 1989, pp. 286–288.

*Primary Examiner*—John E. Chapman
*Attorney, Agent, or Firm*—Jones & Askew

[57] ABSTRACT

An apparatus and method for measuring the volume and calculating the envelope density of an object of known weight. The apparatus has a hollow sample cylinder of known interior diameter mounted to a motor for rotation about its horizontal axis. A dry flowing medium is placed in the sample cylinder and a plunger is removably positioned therein. The plunger is mounted to another drive motor for axial movement within the sample cylinder to compact the dry flowing medium. A load cell connected to the plunger measures the force on the plunger as it advances in the sample cylinder. Control means responsive to the load cell determines the position of the plunger in the sample cylinder at which a known force is exerted on the plunger. The control means also calculates the volume of the dry flowing medium in the sample cylinder both with and without the object positioned therein and divides the difference in the volumes into the weight of the object.

36 Claims, 7 Drawing Sheets

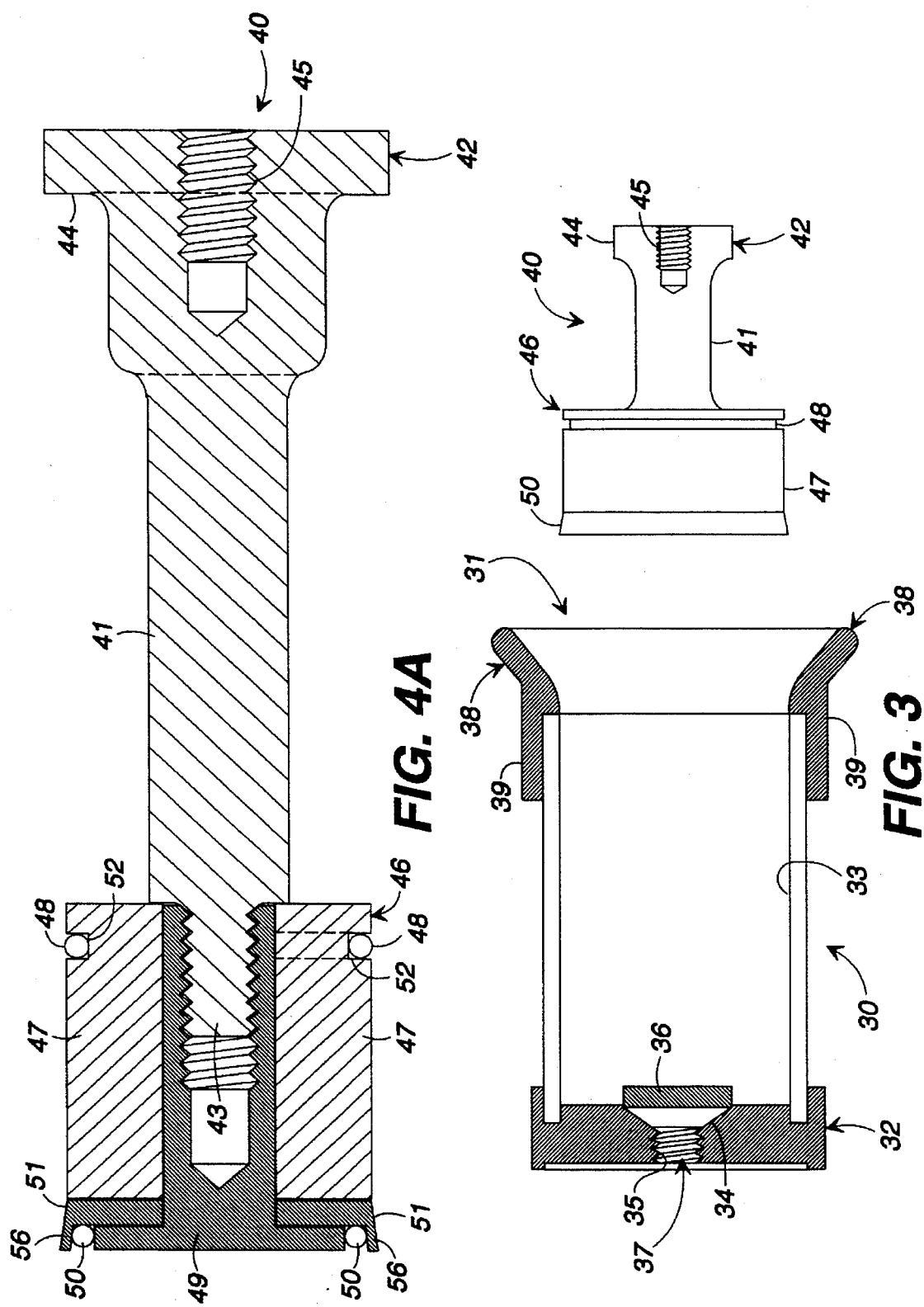

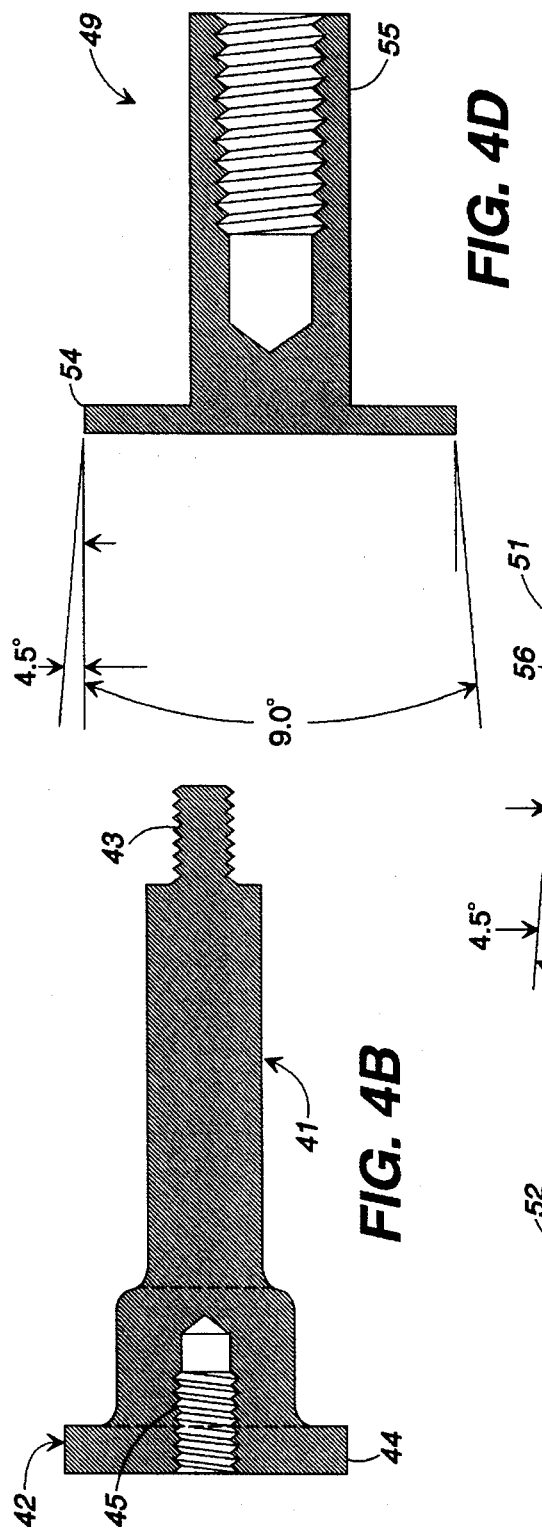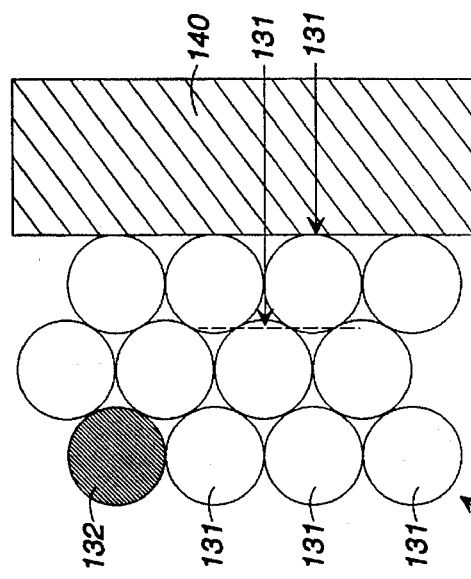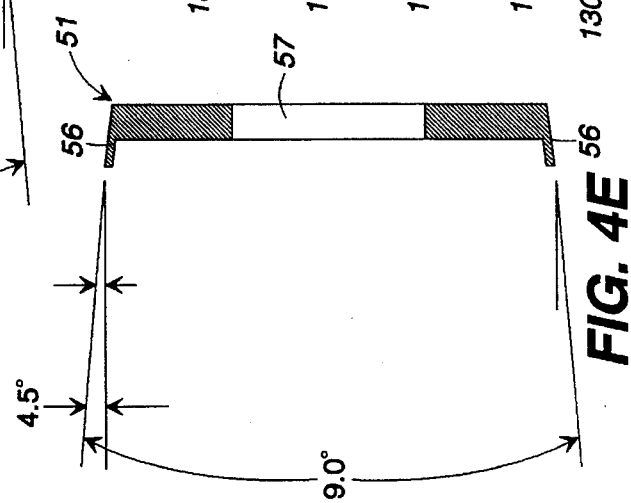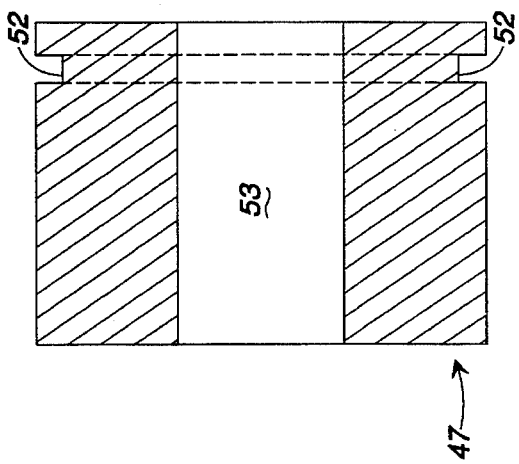
FIG. 4B  FIG. 4C  FIG. 4D  FIG. 4E  FIG. 5

METHOD AND APPARATUS FOR MEASURING ENVELOPE DENSITY

TECHNICAL FIELD

The present invention relates to a method and apparatus for measuring the envelope density of a porous object, and more particularly, to an automated device for determining the envelope density of a porous object with the use of a dry medium.

BACKGROUND OF THE INVENTION

The density of an object is defined as its mass per unit volume (d=m/v). Density is generally stated in terms of grams per cubic centimeter or pounds per cubic foot. The mass of an object is easily established with a balance. The volume of an object is also easily determined if the object is an impervious solid of simple geometric shape. For example, the volume of a cube is the edge length cubed ($L^3$).

Determining the volume of an object of complex shape or an object with holes or pores can be difficult and involve time-consuming measurement techniques. Further, the volume of the object is a matter of definition. The volume of an object can be determined by either excluding the volume of the holes and the pores to find its absolute density (also termed the true or skeletal density) or including the holes and pores up to the point at which they break the plane of the surface to determine the envelope density (also called the bulk or apparent density). Absolute density can be determined by compressing the object until all of the voids are eliminated and only a continuous solid phase remains or by a pycnometer employing helium gas that penetrates the pores of the object.

The present invention is directed towards determining the envelope density of rigid, porous objects. Common rigid, porous objects include everything from sugar cubes and aspirin tablets to floor tiles, concrete, and bakery cookies. Other examples include oil well cores (after the liquid therein is expelled), catalyst pellets, and sintered metal bearings and gears.

The envelope density of an object is valuable when used in conjunction with its absolute density to determine the porosity of that object and its specific pore volume (i.e., the pore space that was eliminated upon compression):

Porosity=[(1- Envelope Density/Absolute Density) 100]%

Pore Volume=[1/Envelope Density - 1/Absolute Density]$cm^3/g$

Porosity and pore volume are parameters that frequently establish the fitness of an object for its intended purpose.

Until recent years, the most widely used technique for assessing external volume involved submerging the test object in mercury and measuring the displaced liquid volume. Testing of this type is described in ASTM Standard Test Method C493-93, entitled "Bulk Density and Porosity of Granular Refractory Materials by Mercury Displacement." Mercury is a non-wetting fluid that bridges the pore entrances and does not penetrate small cracks, holes, or pores. The use of mercury, however, is being phased out because of health concerns. The sample object also becomes contaminated by contact with mercury and must be treated as a hazardous waste.

Another known method requires the porous object to be boiled in water and then remain submerged while the water cools and fills the pores. The sample is first weighed dry, then weighed while suspended in water, and weighed after superficial drying to obtain the desired information. This testing method is described in ASTM Standard Test Method C20-92, entitled "Apparent Porosity, Water Absorption, Apparent Specific Gravity, and Bulk Density of Burned Refractory Brick and Shapes by Boiling Water." A related procedure, ASTM Standard Test Method C830-93, substitutes evacuation for boiling in water and then fills the pores with water or mineral spirits. Both of these methods are tedious and require considerable operator skill to dry the exterior surface of the object while keeping the pores filled with the liquid.

A further method seals off the pores of an object by dipping the object in melted paraffin wax. The wax is not supposed to fill the pores but to seal off the pore entrances. The dry weight, the wax-coated weight in air, and the wax-coated weight suspended in water are used to determine the envelope density. See ASTM Standard Test Method C914-89, entitled "Bulk Density and Volume of Solid Refractories by Wax Immersion." This method is also tedious and can destroy the usefulness of the object because the coating may be impractical to remove.

Attempts have been made in the past to measure the envelope density of an object with the use of dry materials. An example includes British Patent No. 108,512 in which the envelope density of a loaf of bread is determined by filling a container with turnip seeds both with and without the bread present. The envelope density of the loaf is defined as the difference in the volume of the turnip seeds present in the container in both tests. Another method is described in German Patent No. 1,959,681 in which the interior volume of a complex cast iron mold cavity is determined. The cavity is filled with a free flowing powder of known density and then the powder is weighed to determine the cavity volume.

Similar methods include the determination of envelope density of bits of silica gel, carbon, and other particles by placing the particles in a container and filling the container and an extension of it with a fine powder of bronze, steel or zinc. The container and extension are then vibrated vertically and the contents compacted. The extension is removed and the volume of the sample particles is determined by measuring the mass of the powder filling the container with and without the particles present. Results are dependent upon the vigor of the vibration, the excess mass of the powder in the cup extension, and the manual skill of the operator in removing the excess powder.

Finally, the Research and Industrial Corporation of Russia, "TENAKON," describes a device entitled "A Tool for Solid Body Open Porosity Measurement." TENAKON describes a method by which a sample is placed on a vertically moveable piston positioned within a cylinder. A free flowing powder of some sort is then dumped on top of the sample. The cylinder is capped with a cover containing an electrical interrupter switch. The piston moves up and presumably compresses the free-flowing powder until the piston drive is interrupted. No attempt is made to distribute the material around the sample. The volume confined within the cylinder defines the volume of the sample once the free-flowing powder volume is subtracted. It is understood that such a device may be accurate for flat-bottomed samples, but not particularly accurate for crushed or irregular objects.

What is needed, therefore, is a method and apparatus for the measurement of envelope density that provides reliable, reproducible results. These results should be superior to those found with the use of other fluids or known dry medium methods and should not require tedious sample manipulation. The method and apparatus must be easy to use, employ non-hazardous materials, and be non-destructive to the object being tested.

SUMMARY OF THE INVENTION

Generally described, the present invention provides an apparatus and method for measuring the volume and calculating the envelope density of an object of known weight. The apparatus has a hollow sample cylinder of known interior diameter mounted to a motor for rotation about its horizontal axis. A dry flowing medium is placed in the sample cylinder and a plunger is removably positioned therein. The plunger is mounted to another drive motor for axial movement within the sample cylinder to compact the dry flowing medium. A load cell connected to the plunger measures the force on the plunger as it advances in the sample cylinder. Control means responsive to the load cell determines the position of the plunger in the sample cylinder at which a known force is exerted on the plunger. The control means also calculates the volume of the dry flowing medium in the sample cylinder both with and without the object positioned therein and divides the difference in the volumes into the weight of the object.

In a preferred embodiment, the sample cylinder is rotated for forward and reverse agitation to ensure proper flow of the dry flowing medium. The dry flowing medium comprises hard, spherical beads with diameters preferably from about 40 to 250 µm. The dry flowing medium further comprises a small quantity of a flow inducing agent such as graphite. The sample cylinder itself has a porous plate on one end to ensure that air can escape from the cylinder as the plunger advances. The plunger has an outer, polymeric seal, typically of polytetrafluoroethylene or Teflon, to ensure that the beads do not escape behind the plunger.

The drive motor is preferably a stepper motor or a DC motor with an associated encoder. The plunger is mounted to the drive motor by a threaded drive shaft with a known pitch. The control means determines the position of the plunger in the cylinder by counting the number of steps input to the stepper motor or by reading the number of counts produced by the encoder associated with the DC motor.

The control means determines the volume of the dry flowing medium in the sample cylinder, both with and without the object, by measuring the advance of the plunger to the point at which the known force is exerted thereon. The control means then determines the volume of the object by multiplying the difference in the advance of the plunger both with and without the object present therein, by the number of counts per revolution of the stepper motor or the DC motor, the timing belt pulley ratio between the motor and the threaded drive shaft, the number of threads per centimeter of the threaded drive shaft, and the cross-sectional area of the sample cylinder. The control means then multiplies this figure by a near-unity calibration factor to account for force distortions in the dry flowing medium caused by the shape of said object. The apparatus can also calculate the percent porosity and the specific pore volume of the object if supplied with the absolute density information.

It is an object of the present invention to provide an envelope density measurement apparatus.

It is an object of the present invention to provide a method for measuring envelope density.

It is a further object of the present invention to provide a method and apparatus that quickly measures envelope density.

It is a further object of the present invention to provide a method and apparatus for accurately measuring envelope density.

It is a still further object of the present invention to provide a method and apparatus that measures envelope density with repeatable results.

It is a still further object of the present invention to provide an apparatus for the measurement of envelope density that is easy to maintain and highly reliable.

It is a still further object of the present invention to provide an apparatus for the measurement of envelope density that is of compact size and is easy to transport.

It is a still further object of the present invention to provide a method and apparatus that measures envelope density without the use of hazardous materials.

It is a still further object of the present invention to provide a method and apparatus for measuring envelope density that uses a dry flowing medium.

It is a still further object of the present invention to provide a method and apparatus for measuring envelope density that provides an even distribution of a dry flowing medium around a sample.

Other objects, features, and advantages of the present invention will become apparent upon review of the following detailed description of the preferred embodiment of the invention, when taken in conjunction with the drawings and the claims.

BRIEF DESCRIPTION OF THE DRAWINGS

FIG. 3 is a side cross-sectional view of the cylinder and the plunger of FIG. 1.

FIG. 4a is a side cross-sectional view of the plunger.

FIG. 4b is a side cross-sectional view of the stem.

FIG. 4c is a side cross-sectional view of the piston head.

FIG. 4d is a side cross-sectional view of the retainer.

FIG. 4e is a side cross-sectional view of the cup seal.

FIG. 5 is a side cross-sectional view of the beads comprising a bed of a dry flowing medium.

DETAILED DESCRIPTION OF THE INVENTION

The Apparatus

Figure 1:
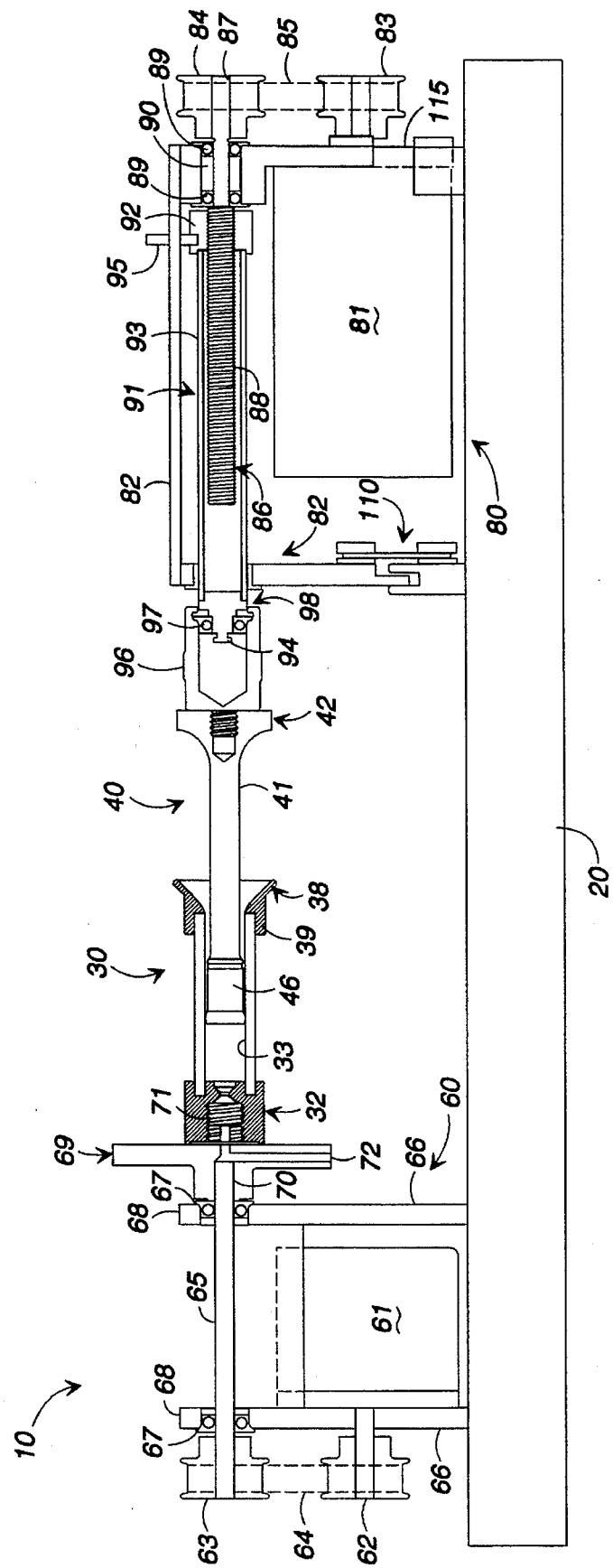
FIG. 1 is a side view showing an envelope density measurement apparatus embodying the invention.
Figure 2:
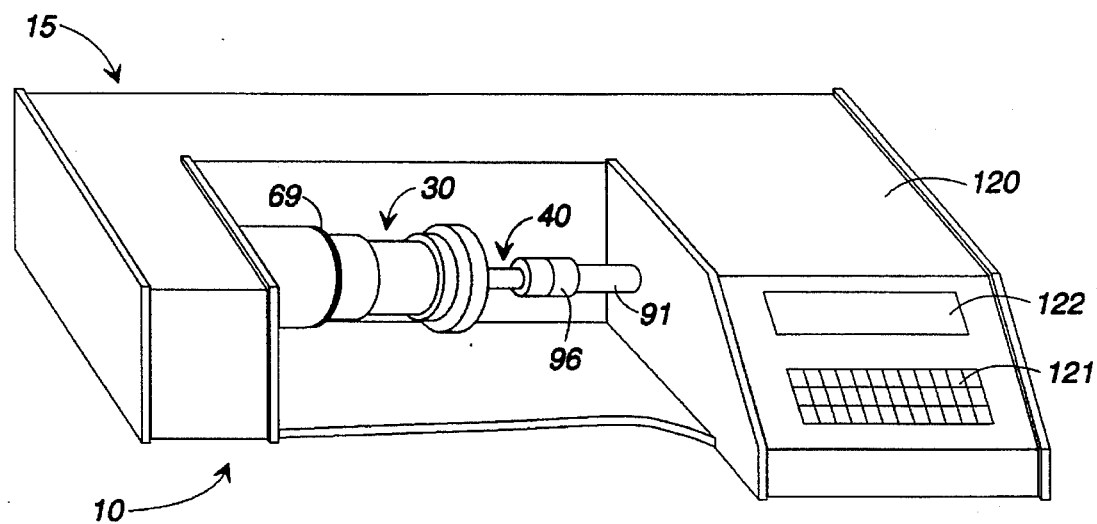
FIG. 2 is a perspective view of a commercial embodiment of the envelope density measurement apparatus.
Figure 6:
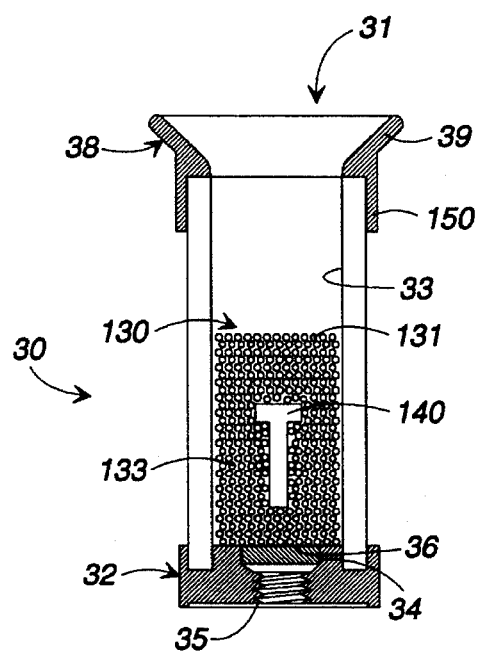
FIG. 6 is a side cross-sectional view of the cylinder with a dry flowing medium (exaggerated) and a sample object therein.

Referring now in more detail to the drawings in which like numerals refer to like parts throughout the several views, FIGS. 1–4 show an envelope density apparatus 10 embodying the present invention. Generally described, the apparatus 10 includes a support base 20, a sample cylinder 30, a plunger 40, a rotating motor assembly 60, a drive motor assembly 80, a load cell 110, and a control means 120. As is shown in FIGS. 5–6, a dry flowing medium 130 is used in the cylinder 30 in determining the envelope density of sample porous objects 140. In a commercial embodiment of the apparatus 10, these parts and assemblies may be contained in a housing 15 as shown in FIG. 2.

Referring to FIGS. 1 and 3, the sample cylinder 30 is preferably bored from a single piece of metal or constructed with a precision-bore glass tube. The diameter of the sample cylinder 30 is preferably consistent within 0.1%. The sample cylinder 30 has an open end 31, a cap 32 enclosing the other end, and a polished interior wall or surface 33. The cap 32 has a tapered opening 34 within the cylinder 30 and a center threaded hole 35 outside of the cylinder 30. The cap 32 is preferably made from stainless steel and is cemented or otherwise fixedly attached to the cylinder 30. A porous plate 36 fills the tapered opening 34 of the cap 32. The porous plate 36 is preferably a flat sintered metal disc. The cap 32 also contains a vent 37 to allow the passage of air out of the cylinder 30 when the plunger 40 is extended therein. The open end 31 of the cylinder 30 preferably extends into a funnel 38. The funnel 38 aids in pouring the medium 130 in and out of the cylinder 30. The funnel 38 may be an integral part of the cylinder 30 or the funnel may be a funnel cap 39, cemented or otherwise fixedly attached to the cylinder 30. The funnel cap 39 defines a flange 150 to provide a mating recess for receiving the open end 31 of the cylinder 30.

A glass-walled cylinder 30 permits viewing the medium 130 and is an advantage when filling or emptying the cylinder 30 or positioning the sample object 140 therein. The cylinder 30 is preferably sized according to the dimensions of the sample object 140. Any conventionally sized cylinder 30 may be used, with cylinder 30 diameters of ½ inch, ¾ inch, 1 inch, 1½ inch, and 2 inches preferred. The length of the cylinder 30 is preferably approximately three times the diameter. The dimensions of the cylinder 30 and the plunger 40 will vary according to the size of the sample object 140.

Referring to FIGS. 1 and 4, the plunger 40 for use with a one inch diameter cylinder 30 is shown. The plunger 40 comprises a stem 41 with an enlarged end 42 at one end and a reduced diameter threaded post 43 at the other. The stem 41 is preferably made from 304 or 316 stainless steel. The enlarged end 42 has a flange 44 with a knurled exterior surface and a threaded central bore 45.

A piston assembly 46 is mounted at the post end of the stem 41. The piston assembly 46 includes a piston head 47, an O-ring 48, a retainer 49, a quad ring 50, and a cup seal 51. The piston head 47 is preferably made from 6061 aluminum. The piston head 45 has a circumferential channel 52 for the insertion of the rubber O-ring 48. The O-ring 48 prevents the plunger 40 from scratching the interior surface 33 of the cylinder 30. The piston head 47 has an internal aperture 53 for receiving the retainer 49.

The retainer 49 has a circular flange 54 from which extends a hollow, internally threaded shaft 55. The retainer 49 is preferably made from 304 or 316 stainless steel. The ends of the flange 54 are angled slightly away from the enlarged end 42 of the stem 41. An angle of approximately 4.5 degrees is preferred. The hollow shaft 55 has an interior diameter sized to mate with the threaded post 43 of the stem 41. The hollow shaft 55 of the retainer 49 is inserted through the aperture 53 of the piston head 47.

The cup seal 51 is circular in shape with an extended lip 56 having a sharp leading edge and an interior bore 57. The interior bore 57 is sized to slide over the hollow shaft 55 of the retainer 49. The extended lip 56 is preferably angled away from the stem 41 by approximately 4.50 degrees. The diametrical compression of the extended lip 56 is about 0.007 inches in this embodiment. The sharp edge on the extended lip 56 prevents particles from wedging past the cup seal 51 and the plunger 40. The cup seal 51 is preferably made from a polymeric substance such as polytetrafluoroethylene ("PTFE") or Teflon.

The piston assembly 46 is assembled by sliding the cup seal 51 down the hollow shaft 55 of the retainer 49. The piston head 47 is also slid down the hollow shaft 55. The rubber quad-ring 50 is inserted between the retainer 49 and the cup seal 51. The quad-ring 50 ensures that the cup seal 51 stays expanded and in contact with the cylinder walls 33. The hollow shaft 55 is then positioned over the threaded shaft 43 of the stem 41 and screwed into place. The rubber O-ring 48 is inserted into the channel 52.

The cylinder 30 is mounted for axial rotation to the rotating motor assembly 60. The rotating motor assembly 60 includes a drive motor 61 mounted to rotating motor assembly support frame 66 by conventional means. The support frame 66 extends upwardly from the base 20. The motor 61 drives a lower timing pulley 62 that, in turn, powers an upper timing pulley 63 via a timing belt 64. The upper timing pulley 63 is mounted on a drive shaft 65. The drive shaft 65 is mounted in a collinear position with respect to the cylinder 30 and the plunger 40. The drive shaft 65 is preferably made from stainless steel. The drive shaft 65 rotates within a pair of bearings 67 packed within retaining rings 68. The retaining rings 68 are mounted on support frame 66 by conventional means.

The drive shaft 65 is connected at the end opposite the upper timing pulley 63 to a wheel-shaped grip 69. The wheel-shaped grip 69 has an aperture 70 on one end for mating with the drive shaft 65 and a hollow, threaded member 71 on the other end for mating with the center threaded hole 35 of the cap 32 of the cylinder 30. The drive shaft 65 mates with the aperture 70 via a set pin (not shown) or other conventional means. The wheel-shaped grip also may include a radial vent hole 72 extending outwardly from the hollow threaded member 71. The radial vent hole 72 communicates with the porous plate 36 of the cap 32 of the cylinder 30 to permit the escape of air from the cylinder 30 as the plunger 40 advances therein. The wheel-shaped grip 69 also has a knurled surface to assist in gripping and turning the grip 69. The wheel-shaped grip 69 is preferably made from 304 or 316 stainless steel.

The rotating motor assembly 60 agitates the cylinder 30 in precession-like fashion by rotating x degrees in one direction and then y degrees in the reverse direction, preferably where x>y. The preferred rotation is for the cylinder 30 to rotate 45 degrees in one direction, reverse 30 degrees in the other direction, and then to repeat this procedure. The drive motor 61 is preferably a stepping motor such as that sold under the trademark "SLO-SYN" by Superior Electric, or a DC motor. The motor 61 preferably rotates the cylinder 30 at approximately 25 rpm and should be capable of quickly reversing direction to produce high accelerations. Other types of manual or mechanical devices can provide the preferred rotation of the cylinder 30.

The plunger 40 is preferably screw driven by the drive motor assembly 80. The drive motor assembly 80 includes a drive motor 81 mounted to a drive motor support frame 82 by conventional means. The support frame 82 extends upwardly from the base 20. The drive motor 81 drives a lower timing pulley 83 that, in turn, drives an upper timing pulley 84 via a timing belt 85. The upper timing pulley 84 is attached by conventional means to a threaded shaft 86. The threaded shaft 86 has a journaled end 87 adjacent to the upper timing pulley 84 and an opposite threaded end 88. The journaled end 87 is mounted in bearings 89 packed within retaining rings 90. The retaining rings 90 are mounted on the support frame 82 by conventional means. The threaded end 88 of the shaft 86 has a preferred pitch of approximately 6.297 threads per centimeter. The threaded shaft 86 is preferably made from 303 stainless steel. There is preferably about a 3 to 1 drive ratio between the motor 81 and threaded shaft 86.

The threaded shaft 86 is positioned within a drive shaft 91. The drive shaft 91 has a threaded ring 92 on the end adjacent to the upper timing pulley 83, an extended hollow cylinder 93, and an enclosed, extended male member 94. The threaded ring 91, the hollow cylinder 93, and the male member 94 are connected via welding or other conventional means or may be formed as an integral piece. The threaded ring 92 has an interior diameter and a pitch to match the diameter and pitch of the threaded end 88 of the shaft 86. The threaded ring 92 has a stop pin 95 extending therefrom. The stop pin 95 rides within a slot (not shown) within the support frame 82 to prevent the drive shaft 91 from rotating. The drive shaft 91 moves horizontally in and out as driven by the threaded shaft 86.

The extended male member 94 of the drive shaft 91 is connected to a bearing bracket 96 via bearings 97. The bearing bracket 96 has a female end 98 and an extended threaded post 99. The bearings 97 are packed in the female end 98 of the bearing bracket 96. The threaded post 99 is attachable to the threaded central bore 45 of the stem 41 of the plunger 40. The bearing bracket 96 is preferably made from 304 or 316 stainless steel. The drive shaft 91 can exert axial force on the plunger 40 via the bearing bracket 96 while the cylinder 30 rotates with the rotating motor assembly 60.

The drive motor 81 may be a stepping motor, such as that sold under the trademark "SLO-SYN" by Superior Electric. A stepping motor 81 of 200 steps per revolution may be used. Alternatively, a DC motor with an associated encoder (not shown) may be used. How far the drive shaft 91 and hence the plunger 40 advances or withdraws is determined by the steps input to the drive motor 81 in combination with the known pitch of the threaded shaft 86 and the drive ratio between the motor 81 and the threaded shaft 86. The advance or retraction of the shaft 86 and the plunger 40 is measured to the nearest 0.000359 centimeter. Other types of manual and mechanical compacting means may be employed.

Mounted to the drive motor assembly support frame 82 is a thin beam load cell 110. The assembly support frame 82 is also supported by two flexible support members 115. The support members 115 are made from thin, flat spring steel. Force exerted upon the plunger 40 through the threaded shaft 86 is thus transmitted to the load cell 110 and the two flexible support members 115. The flexible support members 115 offer negligible resistance to the force in the direction the force is applied, leaving the load cell 110 itself to resist the force. The applied force causes the load cell 110 to bend slightly into an "S" shape which changes its electrical resistance and creates the applied force signal. Other types of manual and mechanical measuring means may be employed.

The Control Means

The operation of the drive motors 61, 81 and the load cell 110 are monitored and controlled by the control means 120. The control means 120 has a Central Processing Unit ("CPU") (not shown) that is a conventional microprocessor. The control means 120, a key pad 121 to accept the various inputs, and a display 122 for the appropriate information. All information will be available by the control means 120 in English, German, French, Spanish, Italian, and other common languages. A printer or RS-232 data channel (not shown) also may be used.

Figure 7A:
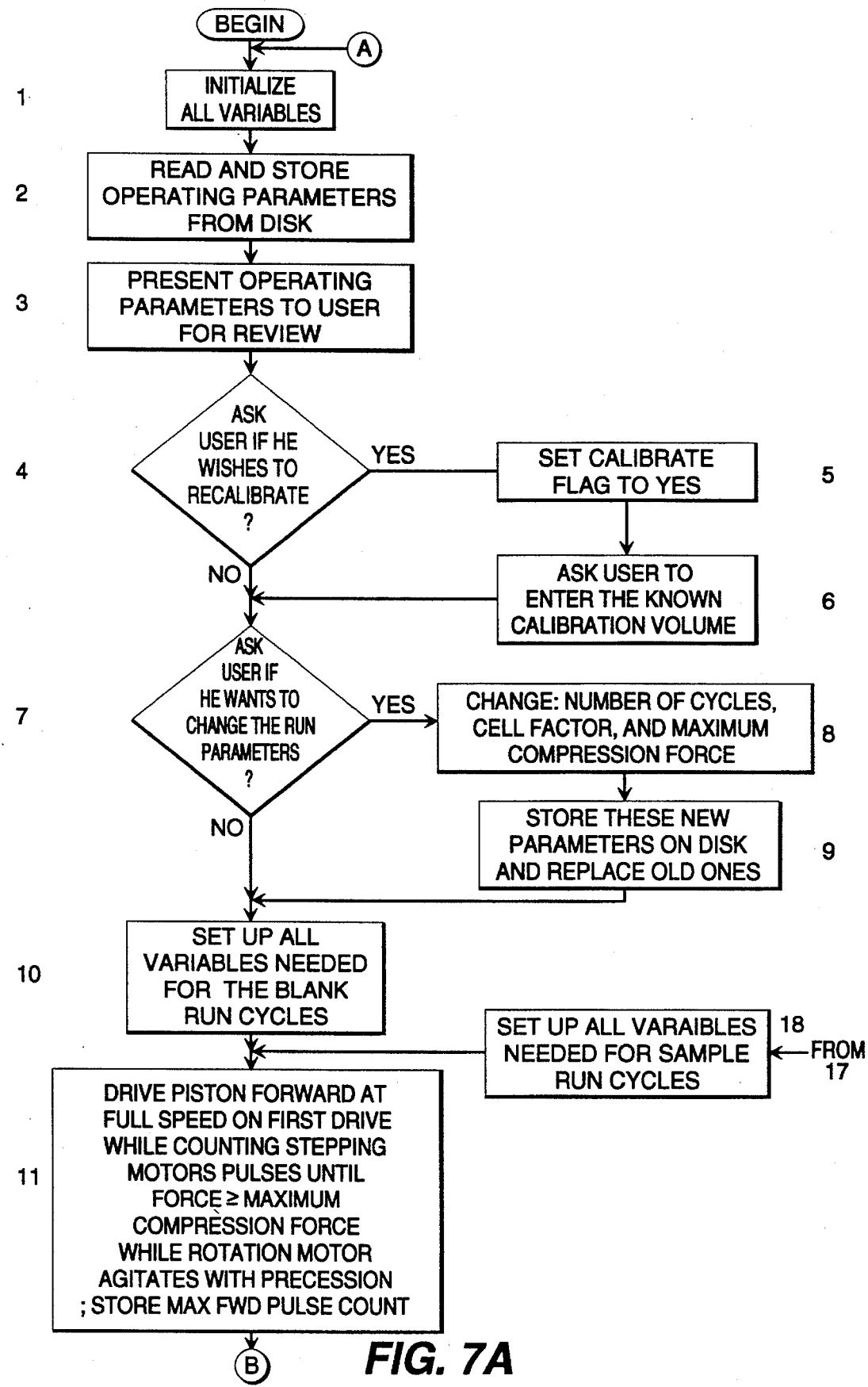
FIG. 7A–C is a flow chart showing the processing steps of the apparatus.
Figure 7B:
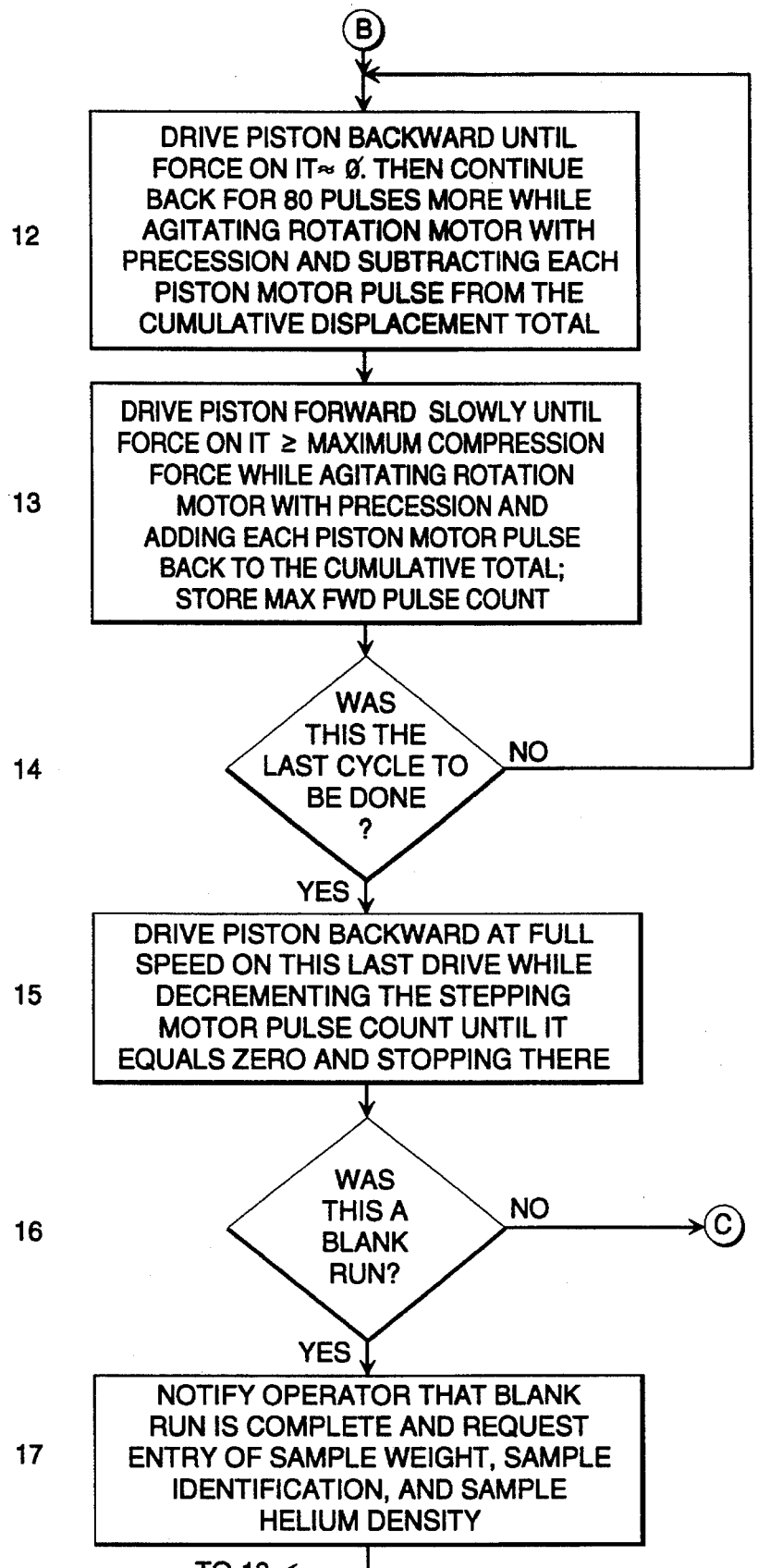
Figure 7C:
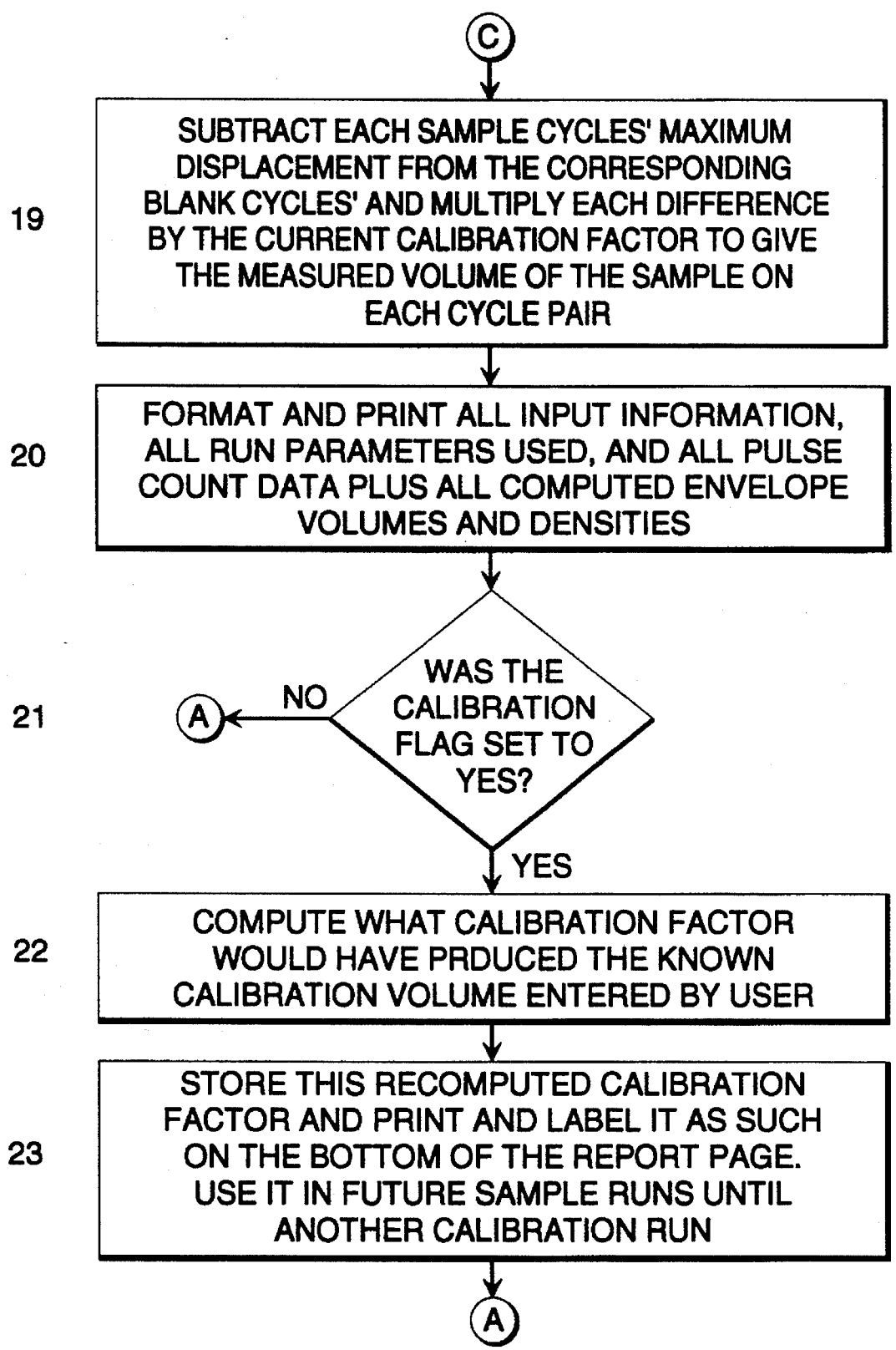

In the preferred embodiment, the system software is coded in the C+ programming language. A detailed flow chart of the preferred operation of the apparatus 10 as performed by the control means 120 is shown in FIG. 7. As an analogy to an electrical circuit diagram, these flow charts are equivalent to a detailed schematic for an electrical circuit where provision of the circuitry for electrical circuit blocks corresponds to provision of actual computer instructions for blocks of the flow chart. Thus, the coding of the process steps of these flow diagrams into instructions for suitable commercially available computers is within the capability of one skilled in the art of programming.

The Dry Flowing Medium

Although a dry medium undergoing compaction does not transmit forces equally in all directions as does a liquid, the use of uniform, small diameter spheres 131 in connection with agitation and stepwise compaction can produce accurate results. The dry flowing medium 130 is preferably a plurality of small, rigid beads 131. Glass, metal, ceramic, plastic or other spherical materials also may be used as the beads 131. These materials generally do not contaminate or destroy the sample object 140. The beads 131 may be hollow depending upon the weight of the material used. The beads 31 are mixed with a flow inducing agent such as graphite 132. The graphite 132 adheres to the bead surface with no dustiness. Some of the graphite 132 also coats the walls 33 of the cylinder 30 and the cup seal 51 of the plunger 40. The dry flowing medium 130 can be reused for multiple tests.

Beads 131 of various sizes and coarseness can be used depending upon the size and nature of the sample object 140. The size of the pores in the object 140 also should be considered in determining the size of the beads 131 to be used. Beads 131 ranging from about 40 to 250 μm may be used. A dry flowing medium 130 with a specific gravity of about 0.7 is recommended when the sample object 140 is lightweight or of low envelope density such as with catalyst substrates and insulating materials. A dry flowing medium 130 with a specific gravity of about 2.5 may be used when testing heavier objects or objects with a high envelope density such as metallic and metal-containing objects.

As is shown in FIG. 5, the first layer of beds 131, whatever the bead size, creates an envelope around the sample object 140. The smaller the diameter of the beads 131, the closer the beads 131 can conform to the shape of the sample object 140. This increased conformity should lead to increased accuracy because larger diameter beads 131 can neither closely outline the periphery of the sample object 140 nor conform to minor indentations in its surface. Because of van der Waals forces, however, compact formation, i.e., cakes of beads 131 that form when compressed under forces generated by the plunger 40, becomes more pronounced and the compacts become more difficult to disperse as bead diameter decreases. The formation of compacts is detrimental to measurement because the formation indicates rigidity in the bed 133 and the inability of the beads 131 to conform to the shape of the objects within the bed 133.

The objective in choosing bead size, therefore is to choose bead sizes that are as small as possible with acceptable flow characteristics. Nearly uniform-sized glass beads 131 of approximately 100 μm in diameter exhibit good flow characteristics, in that they do not give rise to compacts, and give accurate measurements when a proper calibration factor is used.

Operation

The principle upon which the apparatus 10 operates is to confine and consolidate a quantity of the dry flowing medium 130 within the cylinder 30 and then measure the volume of the medium 130. The dry flowing medium 130 is consolidated within the cylinder 30 while undergoing agitation until the predetermined force is reached. The consolidation force applied via the plunger 40 is then released and the sample object 140 (or objects) is inserted into the dry flowing medium 130. Consolidation is again achieved with agitation and the new volume is measured. The difference in the two volumes is taken as the volume of the sample object 140. Multiple tests or "cycles" of both blank and sample runs are preferred for statistically meaningful results. By consolidating the dry flowing medium 130, backing the plunger 40 off a few counts to loosen the medium 130 slightly, advancing the plunger 40 again to consolidate the medium 130 to a further degree, and repeating these steps, the subject invention provides highly reproducible results.

Specifically, how far the plunger 40 moves in terms of driving motor steps or counts until the predetermined force is reached is measured in both a "blank" run and in a sample run. The volume of the sample object 140 is computed from the difference in the steps of the motor 81 in light of the cross-sectional area of the cylinder 30 and the mechanical parameters inherent in driving the plunger 40 with drive motor assembly 80. For example, if the plunger 40 is driven by the motor 81 that registers 200 counts per revolution with the threaded shaft 86 having 6.297 threads per centimeter, and a 3 to 1 drive motor ratio between the motor 81 and threaded shaft 86, and if d is the diameter of the cylinder, the default volume (v) equivalent to one count of the motor 81 is:

$$v=[\pi d^2/((200)(4)(6.297)(3))] \text{cm}^3/\text{count} \qquad \text{Eqn. (1)}$$

The default envelope volume (V) of the sample object 140 is then the difference in the counts with the sample present ($C_{present}$) and with it absent ($C_{absent}$) multiplied by v or:

$$V=[(C_{present}-C_{absent})v] \text{cm}^3 \qquad \text{Eqn. (2)}$$

The apparatus 10 runs three types of tests, a calibration run, a blank run and a sample run. Because, as described above, the dry flowing medium 130 is not quite an ideal fluid, irregular objects in the bed 133 produce small distortions in the internal forces produced within the cylinder 30. The influence of these distorted internal forces can be largely nullified by calibration with another object having known properties and of approximately the same shape as the sample object 140. The calibration object (not shown) is usually a nonporous object because the envelope and absolute densities are identical. If the sample object 140 to be analyzed is truly of unique shape, it may be necessary to fabricate a nonporous calibration object of similar shape. When a calibration test is made with a nonporous sample of known volume V, the above Equation (2) is solved for v. This value of v then becomes the corrected conversion factor for the blank and sample runs.

Finding an object or objects suitable for calibration purposes is generally not difficult. For example, catalysts are usually spherical in shape such that glass or plastic spheres provide a satisfactory calibration object. If the catalysts are in the form of short extrudates, broken glass or plastic rods are satisfactory. Crushed rock or brick pieces are adequately simulated by broken bits of glass. Pharmaceutical tablets and pills can be calibrated by using glass spheres of the same approximate size.

The next step in conducting a test is to choose the appropriately sized cylinder 30 and fill it with the appropriate amount and type of dry flowing medium 130. If enough beads 131 are not employed, the sample object 140 itself will prevent bed compaction. If too many beads 131 are used, the uniformity of the compaction of the bed 133 may be compromised. The sample object 140 preferably should constitute at least about one third of the volume of the final compacted bed 133. Similarly, the cylinder 30 must be of sufficient size to provide the greatest possible shift of the plunger 40 between the blank and sample tests.

It is preferred that the object 140 be centrally positioned within the beads 131 rather than against one end of the cylinder 30. If more than one object 140 is being tested at one time, the objects should be uniformly spread throughout the bed 133. Unlike with vertical rotation where heavy objects tend to position themselves on the bottom of the cylinder 30, objects 140 heavier than the beads 131 generally position themselves centrally in the bed 133 as the cylinder 30 rotates horizontally. Less dense objects 140 readily become submerged within the bed 133 as the test proceeds. If the object 140 has a large central hole, it is best to position the axis of the hole along the axis of the cylinder 30 to ensure compaction of the beads 131 within the hole.

Among the several procedures for conducting a test, the most reliable is to make a blank test and then immediately repeat the test with the sample object 140. This assures that the bed 133 is identical in both cases. As described above, the greatest accuracy is achieved when the apparatus 10 is first calibrated with a calibration object of known properties and having the appropriate size and shape of the sample object 140. The calibration sample is then removed from the bed 133 and the beads 131 are returned to the bed 133 to assure that the force patterns for the blank and sample runs are the same as the calibration run. It is satisfactory to calibrate the apparatus 10 once with a calibration sample and then use approximately the same quantity of identical beads 131 in subsequent tests.

The blank test can be dispensed with if nearly the same bed weight is used in every test and a number of preliminary blank tests covering the possible range of bed weights is made. This data can be stored in the control means 120. Storing the preliminary blank run data and interpolating for the exact weight of each subsequent bed weight may be performed by the control means 120. The composition of the bed should preferably remain the same if a mixture of bead 131 sizes is being used. This may require repeated stirring of the bead mix. The bed weighing procedures should preferably be accurate within 1 milligram to give reproducible results.

A constant force of compaction should preferably be employed in any series of tests in conformity with the requirement for consistency in a procedure. The influence of force on test results is not strong but significant. A force of 2 to 4 pounds is generally applicable with the ½ inch diameter cylinder 30, 10 to 15 pounds is appropriate for the 1 inch cylinder 30, and 25 to 35 pounds should normally be employed for the 2 inch diameter cylinder 30. Applied forces on the bed 133 of these magnitudes are not fully transmitted to the sample object 140 within because some force is used in overcoming the "stiction" force or the force needed to cause the plunger to move while in contact with the walls 33 of the cylinder 30. The additional force needed to overcome the stiction force is added to the entered compaction force. Although distortions are generally not caused to ordinary sample objects 140 during testing, fragile objects should be tested for damage to determine if a reduced force level is necessary.

A constant number of cycles should also be used. Although the first two compaction cycles are likely to be widely variable, the tests thereafter are generally consistent. The present system is programmed to disregard the first two trials. This means that at least three cycles should be employed. A total of seven cycles is preferred to give five good measurements and a fair calculation of standard deviation.

Care should be taken that no beads 131 are lost in inserting or removing the sample object 140. After the media 130 or the media 130 and sample object 140 are positioned in the cylinder 30, the cylinder 30 is positioned such that the plunger 40 is partially inserted therein. The threaded central hole 35 of the cap 32 of the cylinder 30 is then mated with the threaded member 71 of the wheel-shaped grip 69 of the rotating motor assembly 60. The cylinder 30 is removed by reversing this process. The plunger 40 may also be removed by unscrewing the stem 41 of the plunger 40 from the threaded post 99 of the bearing bracket 96.

Referring now to the flow charts of FIG. 7, Steps 1 through 10 involve establishing the appropriate variables for the run. The control means 120 initializes all appropriate variables in step 1 and then reads and stores the operating parameters in step 2. In step 3, the control means 120 presents these parameters to the user for review on the display 122. The operating parameters include run precision in terms of percentage and the maximum number of cycles. Meaningful statistical information usually requires 5 cycles, although any number of cycles between 1 and 25 may be entered. Other run parameters include the amount of consolidation force to be applied in terms of pounds and the calibration factor in terms of cubic centimeters per count.

In step 4, the control means 120 then asks the user if the apparatus 10 is to be re-calibrated. If the user indicates yes, the calibration flag is set to "yes" in step 5 and the control means 120 asks the user for the known calibration volume of the calibration sample in step 6. In step 7, the control means 120 asks the user if the run parameters are to be changed. If the user indicates yes, the user can change, as described above, the number of cycles to be run, the calibration factor, and the maximum compression force in step 8. These parameters are then stored in the control means 120 in step 9. The control means 120 then sets all variable required for a blank run in step 10.

In step 11, the apparatus 10 begins operation. The motor 61 of the rotating motor assembly 60 continually agitates the cylinder 30. The motor 81 of the drive motor assembly 80 drives the plunger 40 forward while the drive motor 81 steps are accounted for by the control means 120. The plunger 40 compacts the dry flowing medium 130 until the predetermined maximum compression force is reached as measured by the load cell 110 at which time the control means 120 stops the motor 81. The maximum forward pulse count of the motor 81 is maintained by the control means 120. In step 12, the plunger 40 is then backed up until the force thereon as determined by the load cell 110 equals zero pounds. The plunger 40 is then withdrawn an additional 80 pulses of the stepper motor 81, or approximately 0.3 mm further. Each stepper motor 81 pulse used to withdraw the plunger 40 is then subtracted from the maximum forward pulse count. The control means 120 maintains the cumulative displacement pulse total. The rotating motor assembly 60 continues to agitate the cylinder 30 while the plunger 40 is withdrawn to permit dilation of the bed 133, or to allow the bed 133 to expand and the individual beads 131 to rearrange their respective positions. This completes one cycle.

In step 13, the plunger 40 is then slowly advanced into the cylinder 30. The plunger 40 is again advanced until the force on the plunger 40 is equal to the predetermined pressure force as measured by the load cell 110. The maximum forward pulse count is again determined and stored in the control means 120. The rotating motor assembly 60 continues to agitate the cylinder 30 during this step. As is shown in step 14, the cycle (steps 12 and 13) is repeated until the maximum number of cycles as input by the user is reached. In step 15, the plunger 40 is again withdrawn until the load thereon reaches zero if the maximum number of cycles has been reached. The number of steps input by the motor 81 are again counted by the control means 120 and subtracted from the cumulative total.

In step 17, if this run was a blank run, the user is notified that the blank run is complete and the control means 120 then requests entry of the weight of sample object 140, sample object 140 identification, and sample object 140 absolute density. These variables are again set in step 18 and steps 11 through 16 are repeated using the sample.

If this was not a blank run, the maximum displacement of each cycle is subtracted from the corresponding blank cycles in step 19. The number of blank cycles should be equal to the maximum number of sample consolidation cycles. Each such sum is then multiplied by the current calibration factor, as in Equation (2), to give the measured volume of the sample 140 on each cycle pair. In step 20, all input information, run parameters, pulse count data, and all computed envelope volumes and densities are formatted and printed. If the absolute density of the sample 140 was entered, the percentage porosity will also be printed. Table I is a sample run report:

TABLE I

Envelope Density Report

Date: 1/1/1996   Time: 10:11:12
Sample: CAT

| Blank Cnt | Sample Cnt | Volume | Density |
|---|---|---|---|
| 9911 | 8994 | 1.927403 | 0.7378323 |
| 10186 | 9305 | 1.851736 | 0.7679821 |
| 10207 | 9317 | 1.870653 | 0.760216 |
| 10217 | 9328 | 1.868551 | 0.761071 |
| 10220 | 9329 | 1.872755 | 0.7593627 |
| 10222 | 9336 | 1.862245 | 0.7636481 |
| 10227 | 9337 | 1.870653 | 0.760216 |

Averages that follow exclude 1st and 2nd cycle data

| | |
|---|---|
| Average envelope volume is: | 1.868971 |
| Average envelope density is: | 0.7608998 |
| Absolute (Helium) density is: | 3.5922 |
| Percent porosity is: | 78.818 |
| Maximum force was: | 10 |
| Sample weight was: | 1.4221 |
| Calibration factor used was: | 2.101857E-03 |

In step 21, if the calibration flag was set, the calibration factor (v) is computed using Equation (2) based upon the known calibration volume entered by the user in step 22. This information is then stored in step 23 and is used as (v) in Equation (2) until the next calibration run.

Results

The typical error from true volume for measurements taken of sample objects 140 by the method described above with approximately 100 μm diameter beads 131 is less than:

$$[\pm(0.02V+d)]cm^3$$

Where V is the true volume of the sample object 140 and d is the diameter of the cylinder 30. The typical error therefore is approximately ±2 percent.

When a calibration object that adequately represents the form and other significant features of the unknown sample object 140 is used, however, the typical resulting error after calibration will be reduced to:

$[\pm(0.01V+d)]cm^3$

The typical error from true volume (V) is therefore approximately ±1 percent. "Typical" as used here shall mean that over 50% of the measurements made on arbitrary selected samples will exhibit errors under the stated limit. The repeatability of measurements taken through successive cycles is generally ±1%. Repeatability depends, in part, upon the size of the cylinder 30 and the volume of the sample object 140.

Although the preferred diameter of the beads 131 appears to be approximately 100 μm, different sizes or even combinations of various sized beads 131 may give superior results depending upon the shape of the object 140.

The foregoing relates only to the preferred embodiments of the present invention, and many changes may be made therein without departing from the scope of the invention as defined by the following claims.

We claim:

1. An apparatus for measuring the envelope density of an object of known weight, comprising:

a hollow sample cylinder of known interior diameter;

said hollow sample cylinder mounted to a motor for rotation about its-horizontal axis;

a dry flowing medium placed in said hollow sample cylinder;

a plunger removably positioned within said hollow sample cylinder;

said plunger mounted to a drive motor for axial movement within said hollow sample cylinder to compact said dry flowing medium;

a load cell connected to said plunger to measure the force on said plunger as it advances in said hollow sample cylinder; and control means responsive to said load cell for:

determining the position of said plunger in said hollow sample cylinder at which a known force is exerted on said plunger; and calculating the volume of said dry flowing medium in said hollow sample cylinder both with and without said object positioned in said dry flowing medium and dividing the difference in said volumes into said weight of said object.

2. The envelope density measurement apparatus of claim 1, wherein said rotation of said hollow sample cylinder comprises rapid forward and reverse agitation.

3. The envelope density measurement apparatus of claim 1, wherein said dry flowing medium comprises uniform-sized beads.

4. The envelope density measurement apparatus of claim 1, wherein said dry flowing medium comprises beads with a diameter from about 40 to 250 μm.

5. The envelope density measurement apparatus of claim 4, wherein said beads are approximately 100 μm in diameter.

6. The envelope density measurement apparatus of claim 1, wherein said dry flowing medium comprises hollow beads with a specific gravity of approximately 0.7 for use with said sample objects of low density.

7. The envelope density measurement apparatus of claim 1, wherein said dry flowing medium further comprises a flow inducing agent.

8. The envelope density measurement apparatus of claim 7, wherein said flow inducing agent comprises graphite.

9. The envelope density measurement apparatus of claim 1, wherein said plunger has an outer seal comprising polytetrafluorethylene.

10. The envelope density measurement apparatus of claim 1, wherein sample cylinder further comprises means for venting air out of said cylinder.

11. The envelope density measurement apparatus of claim 1, wherein said control means determines said volume of said dry flowing medium in said hollow sample cylinder by measuring the advance of said plunger to said position of said plunger at which said known force is exerted on said plunger.

12. The envelope density measurement apparatus of claim 1, wherein said control means further multiplies said difference in said volume of said dry flowing medium with and without said object positioned in said dry flowing medium in said sample cylinder by a calibration factor to account for force distortions in said dry flowing medium caused by the shape of said object.

13. The envelope density measurement apparatus of claim 1, wherein said control means further calculates the percent porosity of said object.

14. The envelope density measurement apparatus of claim 1, wherein said drive motor is a stepper motor.

15. The envelope density measurement apparatus of claim 14, wherein said control means determines said position of said plunger by counting the number of steps input to said stepper motor.

16. The envelope density measurement apparatus of claim 15, wherein said plunger is screw driven by a threaded drive shaft powered by said drive motor.

17. The envelope density measurement apparatus of claim 16, wherein said control means determines said volume of said object by multiplying said difference in said advance of said plunger, until said known force on said plunger is reached, both with and without said object present therein, by the number of counts per revolution of said stepper motor, the number of threads per centimeter of said threaded drive shaft, the drive ratio between said motor and said threaded drive shaft, and the cross-sectional area of said sample cylinder.

18. The envelope density measurement apparatus of claim 1, wherein said drive motor is a DC motor with an associated encoder.

19. The envelope density measurement apparatus of claim 18, wherein said control means determines said position of said plunger by reading the number of counts produced by said encoder associated with said DC motor.

20. An apparatus for measuring the envelope density of an object of known weight, comprising:

a hollow sample cylinder of known interior diameter;

said hollow sample cylinder mounted to a motor for forward and reverse agitation about its horizontal axis;

a plurality of fine, spherical beads placed in said hollow sample cylinder;

a plunger removably positioned within said hollow sample cylinder;

said plunger mounted to a stepper motor for movement within said hollow sample cylinder to compact said fine, spherical beads;

a load cell connected to said plunger to measure the force on said plunger as it advances in said hollow sample cylinder; and control means responsive to said load cell for:

determining a position of said plunger in said hollow sample cylinder at which a known force is exerted on said plunger; and calculating the volume of said fine, spherical beads in said hollow sample cylinder by measuring the advance of said plunger to said position of said plunger at which said known force is exerted on said plunger both with and without said object positioned in said fine, spherical beads and dividing the difference in said volumes into said weight of said object.

21. The envelope density measurement apparatus of claim 20, wherein said fine, spherical beads comprise uniform sized beads.

22. The envelope density measurement apparatus of claim 20, wherein said fine, spherical beads have a diameter from about 40 to 250 μm.

23. The envelope density measurement apparatus of claim 22, wherein said fine, spherical beads are approximately 100 μm in diameter.

24. The envelope density measurement apparatus of claim 20, wherein said fine, spherical beads comprises a specific gravity of approximately 0.7 for use with said sample objects of low density.

25. The envelope density measurement apparatus of claim 20, wherein said control means determines said position of said plunger by counting the number of steps input to said stepper motor.

26. The envelope density measurement apparatus of claim 20, wherein said control means further multiplies said difference in said volume of said dry flowing medium with and without said object positioned in said dry flowing medium in said sample cylinder by a calibration factor to account for force distortions in said dry flowing medium caused by the shape of said object.

27. The envelope density measurement apparatus of claim 20, wherein said plunger is screw driven by a threaded drive shaft powered by said drive motor.

28. The envelope density measurement apparatus of claim 20, wherein said control means determines said volume of said object by multiplying said difference in said advance of said plunger, until said known force on said plunger is reached, both with and without said object present therein, by the number of counts per revolution of said stepper motor, the number of threads per centimeter of said threaded drive shaft, the drive ratio between said motor and said threaded drive shaft, and the cross-sectional area of said sample cylinder.

29. An apparatus for measuring the volume of an object, comprising:

a hollow sample cylinder of known interior diameter;

said hollow sample cylinder mounted to a motor horizontally for forward and reverse agitation about its longitudinal axis;

a dry flowing medium placed in said hollow sample cylinder;

a plunger removably positioned within said hollow sample cylinder;

said plunger mounted to a drive motor for horizontal movement within said hollow sample cylinder to compact said dry flowing medium;

a load cell connected to said plunger to measure the force on said plunger as it advances in said hollow sample cylinder; and control means to calculate the advance of said plunger both with and without said object positioned in said dry flowing medium until said force thereon reaches a predetermined limit as measured by said load cell.

30. An apparatus for obtaining information related to the volume of an object, comprising:

a hollow sample cylinder of known interior diameter capable of receiving said object;

means for rotating said hollow sample cylinder about its longitudinal axis;

a dry flowing medium placed in said hollow sample cylinder;

a plunger removably positioned within said hollow sample cylinder;

means for moving said plunger within said hollow sample cylinder to compact said dry flowing medium;

means for measuring the force on said plunger as it advances in said hollow sample cylinder; and means for monitoring the position of said plunger at which at least one level of force is applied.

31. A method for determining the envelope density of an object of known weight, comprising the steps of:

rotating about its longitudinal axis a cylinder of known interior diameter;

measuring the advance of a plunger against a dry flowing medium contained in said cylinder until a known force is placed on said plunger;

determining the volume of said dry flowing medium in said cylinder;

placing said object into said dry flowing medium in said cylinder;

measuring the advance of said plunger in said cylinder with said object positioned in said dry flowing medium until said known force on said plunger is reached;

determining the volume of said dry flowing medium in said cylinder with said object positioned therein;

calculating the difference between said volume of said dry flowing medium in said cylinder with and without said object positioned therein and dividing this sum into said weight of said object.

32. The method of claim 31, wherein said step of rotating comprises agitating said cylinder by alternatively rotating said cylinder in forward and reverse directions.

33. The method of claim 31, wherein said plunger is advanced by a stepping motor and wherein said steps of measuring said advance of said of said plunger comprise measuring the steps input to said stepper motor.

34. The method of claim 31, further comprising multiple testing cycles wherein each said cycle comprises said steps of rotating, measuring, and determining said volume of said dry flowing medium in said cylinder, both with and without said object therein, and calculating said difference between said volume of said dry flowing medium both with and without said object therein, and further comprising excluding the first two of said testing cycles.

35. A method for determining the volume of an object, comprising the steps of:

rotating about its longitudinal axis a cylinder of known interior diameter;

measuring the advance of a plunger against a dry flowing medium contained in said cylinder until a known amount of force is placed on said plunger;

determining the volume of said dry flowing medium in said cylinder;

placing said object into said dry flowing medium in said cylinder;

measuring the advance of said plunger in said cylinder with said object positioned in said dry flowing medium until said known amount of force on said plunger is reached;

determining the volume of said dry flowing medium in said cylinder with said object positioned therein;

calculating the difference between said volume of said dry flowing medium in said cylinder with and without said object positioned therein.

36. The method of claim 35, further comprising multiple testing cycles wherein each said cycle comprises said steps of rotating, measuring, and determining said volume of said dry flowing medium in said cylinder, both with and without said object therein, and calculating said difference between said volume of said dry flowing medium both with and without said object therein, and further comprising excluding the first two of said testing cycles.

* * * * *